(12) United States Patent
Wright et al.

(10) Patent No.: US 8,461,105 B2
(45) Date of Patent: *Jun. 11, 2013

(54) POLYMER-BASED SUSTAINED RELEASE DEVICE

(75) Inventors: Steven G. Wright, Madeira, OH (US); Troy Christensen, Mason, OH (US); Thean Yeoh, Salem, CT (US); Michael E. Rickey, Morrow, OH (US); Joyce M. Hotz, Cincinnati, OH (US); Rajesh Kumar, Marlborough, MA (US); Henry R. Costantino, Woodinville, WA (US)

(73) Assignee: Alkermes Pharma Ireland Limited, Dublin (IE)

( * ) Notice: Subject to any disclaimer, the term of this patent is extended or adjusted under 35 U.S.C. 154(b) by 805 days.

This patent is subject to a terminal disclaimer.

(21) Appl. No.: 12/585,574

(22) Filed: Sep. 17, 2009

(65) Prior Publication Data

US 2010/0152111 A1 Jun. 17, 2010

Related U.S. Application Data

(63) Continuation of application No. 11/826,535, filed on Jul. 16, 2007, now Pat. No. 7,612,176, which is a continuation of application No. 11/104,877, filed on Apr. 13, 2005, now Pat. No. 7,456,254.

(60) Provisional application No. 60/563,245, filed on Apr. 15, 2004.

(51) Int. Cl.
*A61K 38/00* (2006.01)
*C07K 14/00* (2006.01)

(52) U.S. Cl.
USPC ............................. 514/2; 530/300; 424/489

(58) Field of Classification Search
None
See application file for complete search history.

(56) References Cited

U.S. PATENT DOCUMENTS

| | | |
|---|---|---|
| 3,523,906 A | 8/1970 | Vrancken et al. |
| 3,691,090 A | 9/1972 | Kitajima et al. |
| 3,737,337 A | 6/1973 | Schnoring et al. |
| 3,891,570 A | 6/1975 | Fukushima et al. |
| 3,960,757 A | 6/1976 | Morishita et al. |
| 4,389,330 A | 6/1983 | Tice et al. |
| 4,530,840 A | 7/1985 | Tice et al. |
| 4,840,896 A | 6/1989 | Reddy et al. |
| 4,923,805 A | 5/1990 | Reddy et al. |
| 5,019,400 A | 5/1991 | Gombotz et al. |
| 5,126,147 A | 6/1992 | Silvestri et al. |
| 5,204,108 A | 4/1993 | Illum |
| 5,225,205 A | 7/1993 | Orsolini |
| 5,271,945 A | 12/1993 | Yoshioka et al. |
| 5,312,335 A | 5/1994 | McKinnon et al. |
| 5,336,505 A | 8/1994 | Ng et al. |
| 5,385,887 A | 1/1995 | Yim et al. |
| 5,424,286 A | 6/1995 | Eng |
| 5,589,167 A | 12/1996 | Cleland et al. |
| 5,630,796 A | 5/1997 | Bellhouse et al. |
| 5,639,640 A | 6/1997 | Reddy et al. |
| 5,656,297 A | 8/1997 | Bernstein et al. |
| 5,672,549 A | 9/1997 | Minami et al. |
| 5,707,644 A | 1/1998 | Illum |
| 5,767,251 A | 6/1998 | Reddy et al. |
| 5,922,253 A | 7/1999 | Herbert et al. |
| 5,981,719 A | 11/1999 | Woiszwillo et al. |
| 6,113,947 A | 9/2000 | Cleland et al. |
| 6,120,787 A | 9/2000 | Gustafsson et al. |
| 6,190,702 B1 | 2/2001 | Takada et al. |
| 6,194,006 B1 | 2/2001 | Lyons et al. |
| 6,217,893 B1 | 4/2001 | Pellet et al. |
| 6,284,283 B1 | 9/2001 | Costantino et al. |
| 6,368,630 B1 | 4/2002 | Bernstein et al. |
| 6,369,116 B1 | 4/2002 | Wong et al. |
| 6,465,425 B1 | 10/2002 | Tracy et al. |
| 6,475,507 B1 | 11/2002 | Pellet et al. |
| 6,479,065 B2 | 11/2002 | Jaworowicz et al. |
| 6,495,164 B1 | 12/2002 | Ramstack et al. |
| 6,506,724 B1 | 1/2003 | Hiles et al. |
| 6,548,302 B1 | 4/2003 | Mao et al. |
| 6,558,702 B2 | 5/2003 | Dasch et al. |
| 6,749,866 B2 | 6/2004 | Bernstein et al. |
| 6,824,822 B2 | 11/2004 | Rickey et al. |
| 7,164,005 B2 | 1/2007 | Costantino et al. |
| 7,456,254 B2 | 11/2008 | Wright et al. |
| 7,462,365 B2 * | 12/2008 | Costantino et al. ........... 424/468 |
| 7,563,871 B2 | 7/2009 | Wright et al. |
| 7,612,176 B2 | 11/2009 | Wright et al. |
| 2003/0003074 A1 | 1/2003 | Zentner et al. |
| 2003/0004100 A1 | 1/2003 | Dasch et al. |
| 2003/0087820 A1 | 5/2003 | Young et al. |
| 2003/0118660 A1 | 6/2003 | Rickey et al. |
| 2003/0133979 A1 | 7/2003 | Burke et al. |
| 2004/0047863 A1 | 3/2004 | Bendele et al. |
| 2004/0121009 A1 | 6/2004 | Dasch et al. |

(Continued)

FOREIGN PATENT DOCUMENTS

| | | |
|---|---|---|
| EP | 0 052 510 | 5/1982 |
| EP | 0 302 582 B1 | 2/1989 |

(Continued)

OTHER PUBLICATIONS

Carrasquillo, et al., "Non-aqueous encapsulation of excipient-stabilized spray-freeze dried BSA into poly(lactide-co-glycolide) microspheres results in release of native protein," Journal of Controlled Release 76: 199-208 (2001).

Castellanos, et al., "Prevention of structural perturbations and aggregation upon encapsulation of bovine serum albumin into poly(lactide-co-glycolide) microspheres using the solid-in-oil-in-water technique," Journal of Pharmacy and Pharmacology 53: 1099-1107 (2001).

(Continued)

*Primary Examiner* — Anand Desai
(74) *Attorney, Agent, or Firm* — Covington & Burling LLP; Andrea G. Reister; Melody Wu

(57) ABSTRACT

This invention relates to compositions for the sustained release of biologically active polypeptides, and methods of forming and using said compositions, for the sustained release of biologically active polypeptides. The sustained release compositions of this invention comprise a biocompatible polymer having dispersed therein, a biologically active polypeptide and a sugar.

5 Claims, 10 Drawing Sheets

U.S. PATENT DOCUMENTS

| | | | |
|---|---|---|---|
| 2004/0208929 A1 | 10/2004 | Costantino et al. | |
| 2004/0228833 A1 | 11/2004 | Costantino et al. | |
| 2005/0271702 A1 | 12/2005 | Wright et al. | |
| 2006/0110423 A1 | 5/2006 | Wright et al. | |
| 2007/0166352 A1 | 7/2007 | Wright et al. | |
| 2008/0125348 A1 | 5/2008 | Wright et al. | |
| 2008/0260847 A1 | 10/2008 | Wright et al. | |
| 2009/0247463 A1 | 10/2009 | Wright et al. | |
| 2010/0152097 A1* | 6/2010 | Wright et al. | 514/2 |

FOREIGN PATENT DOCUMENTS

| | | |
|---|---|---|
| EP | 0 521 586 A1 | 1/1993 |
| JP | 2-124814 A | 5/1990 |
| JP | 7-196479 A | 8/1995 |
| RU | 2198678 C2 | 2/2003 |
| WO | WO-90/13285 A1 | 11/1990 |
| WO | WO-90/13780 A1 | 11/1990 |
| WO | WO-92/19241 | 11/1992 |
| WO | WO-96/36317 A1 | 11/1996 |
| WO | WO-97/31943 A1 | 9/1997 |
| WO | WO-97/41837 | 11/1997 |
| WO | WO-00/59476 A1 | 10/2000 |
| WO | WO-01/19345 A1 | 3/2001 |
| WO | WO-01/28525 A2 | 4/2001 |
| WO | WO-02/083096 A | 10/2002 |
| WO | WO-03/020245 A1 | 3/2003 |
| WO | WO-03/066585 A2 | 8/2003 |
| WO | WO-2004/034975 A2 | 4/2004 |
| WO | WO-2004/035754 A2 | 4/2004 |
| WO | WO-2004/035762 A2 | 4/2004 |
| WO | WO-2004/036186 A2 | 4/2004 |
| WO | WO-2004/103342 A2 | 12/2004 |

OTHER PUBLICATIONS

Costantino, et al., "Protein Spray Freeze Drying. 2. Effect of formulation variables on particle size and stability," J. Pharm. Sci., 91: 388-395 (2002).

Costantino, et al., "Relationship between encapsulated drug particle size and initial release of recombinant human growth hormone from biodegradable microspheres," J. Pharm. Sci., 93(10): 2624-2634 (2004).

Creighton, Proteins: Structures and Molecular Principles (pub., W.H. Freeman and Company, New York, NY), pp. 149-150 (1984).

Elvassore, et al., "Production of Insulin-Loaded Poly(Ethylene Glycol)/Poly(l-Lactide) (PEG/PLA) Nanoparticles by Gas Antisolvent Techniques," J. of Pharmaceutical Sci., 90(10): 1628 (Oct. 2001).

Lee and Timasheff, "The stabilization of proteins by sucrose," J. Biological Chem., 256(14): 7193-7201 (Jul. 1981).

Lucke, et al., "Peptide Acylation by Poly($\alpha$-Hydroxy Esters)," Pharmaceutical Research, 19(2): 175-181 (2002).

Mehta, et al., "Peptide containing microspheres from low molecular weight and hydrophilic poly(*d,l* -lactide-co-glycolide)," Journal of Coltrolled Release, 41: 249-257 (1996).

Perez, et al., "Recent trends in stabilizing protein structure upon encapsulation and release from bioerodible polymers," Journal of Pharmacy and Pharmacology, 54(3): 301-313 (Mar. 2002).

Szayna, et al., "Exendin-4 Decelerates Food Intake, Weight Gain, and Fat Deposition in Zucker Rats," Endocrinology, 141(6): 1936-1941 (2000).

Taylor, et al., "Continuous Subcutaneous Infusion of AC2993 (Synthetic Exendin-4) Provides Sustained Day-Long Glycemic Control to Patients with Type 2 Diabetes," Diabetes 51 (Suppl 2): A85 (Jun. 2002 Conference Abstract).

Thomasin, et al., "A Contribution to Overcoming the Problem of Residual Solvents in Biodegradable Microspheres Prepared by Coacervation," Eur. J. Pharm. Biopharm. 42(1): 16-24 (1996).

van Santbrink and Fauser, "Urinary follicle-stimulating hormone for normogonadotropic colomiphene-resistant anovulatory infertility: Prospective, randomized comparison between low dose step-up and step-down dose regimens," J. Clin. Endocrin. Metab., 82(11): 3597-3602 (1997).

Wang, et al., "Glucagon-like peptide-1 treatment delays the onset of diabetes in 8 week-old *db/db* mice," Diabetolo 45: 1263-1273 (2002).

* cited by examiner

POLYMER-BASED SUSTAINED RELEASE DEVICE

BACKGROUND OF THE INVENTION

Numerous proteins and peptides, collectively referred to herein as polypeptides, exhibit biological activity in vivo and are useful as medicaments. Many illnesses or conditions require administration of a sustained level of medicament to provide the most effective prophylactic and/or therapeutic effects. Sustained levels are often achieved by the administration of biologically active polypeptides by frequent subcutaneous injections, which often results in fluctuating levels of medicament and poor patient compliance.

As an alternative, the use of biodegradable materials, such as polymers, encapsulating the medicament can be employed as a sustained delivery system. The use of biodegradable polymers, for example, in the form of microparticles or microcarriers, can provide a sustained release of medicament, by utilizing the inherent biodegradability of the polymer to control the release of the medicament thereby providing a more consistent, sustained level of medicament and improved patient compliance.

However, these sustained release devices can often exhibit high initial bursts of medicament and minimal release thereafter, resulting in serum drug levels outside the therapeutic window and/or poor bioavailability of the medicament. In addition, the presence of polymer, physiological temperatures and body response to the sustained release composition can cause the medicament to be altered (e.g., degraded, aggregated) thereby interfering with the desired release profile for the medicament.

Further, methods used to form sustained release compositions can result in loss of activity of the medicament due to the instability of the medicament and the degradative effects of the processing steps. Degradative effects are particularly problematic when the medicament is a polypeptide.

Therefore, a need exists for a means of administering biologically active polypeptides in a sustained fashion wherein the amount of polypeptide delivered is at therapeutic levels, and retains activity and potency for the desired period of release. While much work has been developed that addresses these problems, novel solutions are required.

SUMMARY OF THE INVENTION

The invention relates to the discovery that superior release profiles (such as those characterized by a ratio of $C_{max}$ to $C_{ave}$ of about 3 or less) can be achieved with a formulation containing few components by optimizing the silicone oil to polymer ratio in the manufacturing process, thereby achieving a low pore volume. This invention relates to compositions for the sustained release of agents, such as biologically active polypeptides, and methods of forming and using such compositions, for the sustained release of biologically active polypeptides. The sustained release compositions of this invention comprise a biocompatible polymer, an agent, such as a biologically active polypeptide, and a sugar. The polypeptide and sugar are preferably dispersed in the polymer. The polypeptide and sugar can be dispersed separately or, preferably, together. The sustained release composition provides a desirable and consistent release profile. In a particular embodiment, the profile is characterized as having a ratio of $C_{max}$ to $C_{ave}$ of about 3 or less. In a preferred embodiment, the biologically active polypeptide is an antidiabetic or glucoregulatory polypeptide, such as GLP-1, GLP-2, exendin-3, exendin-4 or an analog, derivative or agonist thereof, preferably exendin-4. The sugar is preferably sucrose, mannitol or a combination thereof. A preferred combination includes exendin-4 and sucrose and/or mannitol.

Additionally or alternatively, the sustained release composition comprises a biocompatible polymer, an agent, such as a biologically active polypeptide and a sugar wherein the composition has a total pore volume of about 0.1 mL/g or less. In a specific embodiment, the total pore volume is determined using mercury intrusion porosimetry.

Additionally or alternatively, the sustained release composition consists essentially of or, alternatively consists of, a biocompatible polymer, exendin-4 at a concentration of about 3% w/w and sucrose at a concentration of about 2% w/w. The biocompatible polymer is preferably a poly lactide coglycolide polymer.

The invention also includes a method for forming compositions for the sustained release of biologically active agents, such as polypeptides, which comprises forming a mixture by combining an aqueous phase comprising water, an agent, such as a water soluble polypeptide, and a sugar with an oil phase comprising a biocompatible polymer and a solvent for the polymer; forming a water-in-oil emulsion by, for example, sonicating or homogenizing, the mixture; adding silicone oil to the mixture to form embryonic microparticles; transferring the embryonic microparticles to a quench solvent to harden the microparticles; collecting the hardened microparticles; and drying the hardened microparticles. In a particular embodiment, the silicone oil is added in an amount sufficient to achieve a silicone oil to polymer solvent ratio of about 1.5:1. Additionally or alternatively, the polymer is present in the oil phase at about 10% w/v or less.

The agent or polypeptide, e.g. exendin-4, can be present in the composition described herein at a concentration of about 0.01% to about 10% w/w based on the total weight of the final composition. In addition, the sugar, e.g. sucrose, can be present in a concentration of about 0.01% to about 5% w/w of the final weight of the composition.

The composition of this invention can be administered to a human, or other animal, by injection, implantation (e.g., subcutaneously, intramuscularly, intraperitoneally, intracranially, and intradermally), administration to mucosal membranes (e.g., intranasally, intravaginally, intrapulmonary or by means of a suppository), or in situ delivery (e.g., by enema or aerosol spray).

When the sustained release composition has incorporated therein a hormone, particularly an anti-diabetic or glucoregulatory peptide, for example, GLP-1, GLP-2, exendin-3, exendin-4 or agonists, analogs or derivatives thereof, the composition is administered in a therapeutically effective amount to treat a patient suffering from diabetes mellitus, impaired glucose tolerance (IGT), obesity, cardiovascular (CV) disorder or any other disorder that can be treated by one of the above polypeptides or derivatives, analogs or agonists thereof.

The use of a sugar in the sustained release compositions of the invention improves the bioavailability of the incorporated biologically active polypeptide, e.g, anti-diabetic or glucoregulatory peptides, and minimizes loss of activity due to instability and/or chemical interactions between the polypeptide and other components contained or used in formulating the sustained release composition, while maintaining an excellent release profile.

The advantages of the sustained release formulations as described herein include increased patient compliance and acceptance by eliminating the need for repetitive administration, increased therapeutic benefit by eliminating fluctuations in active agent concentration in blood levels by providing a desirable release profile, and a potential lowering of the total amount of biologically active polypeptide necessary to provide a therapeutic benefit by reducing these fluctuations.

DETAILED DESCRIPTION OF THE INVENTION

Figure 1:
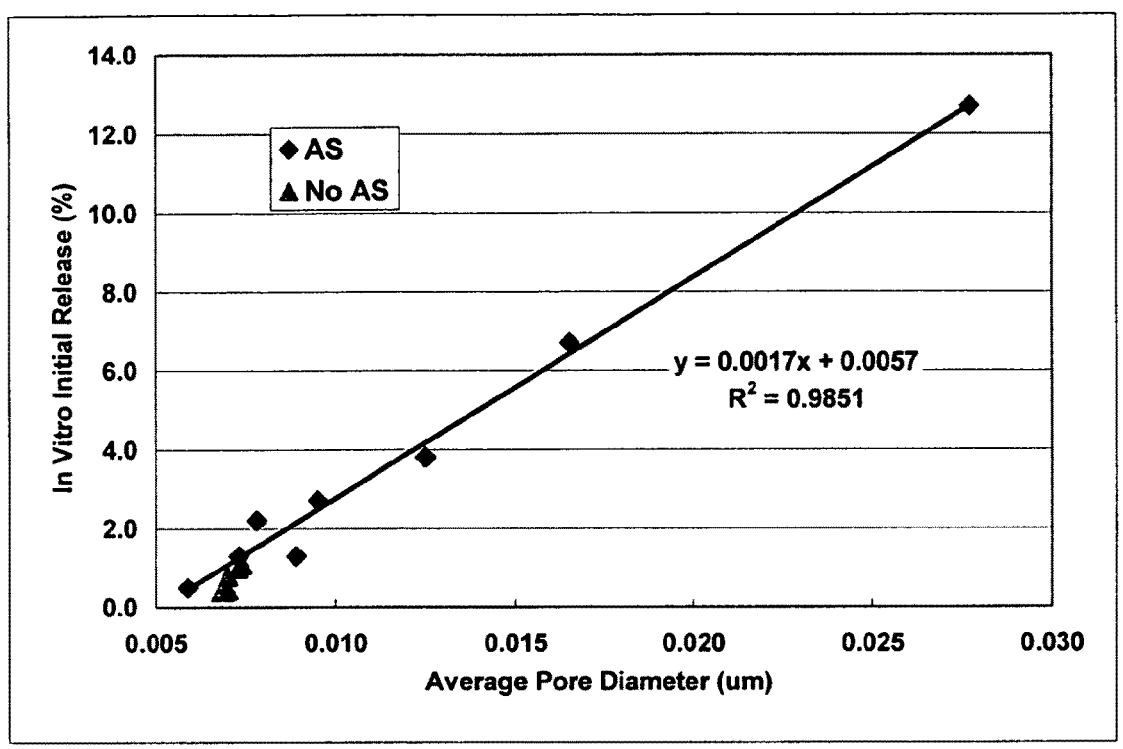
FIG. 1 is a graph showing the relationship between the average pore diameter and the in vitro release for sustained release compositions described herein (A.S.=Ammonium Sulfate).

This invention relates to compositions for the sustained release of biologically active polypeptides, and methods of forming and using said compositions, for the sustained release of biologically active polypeptides. The sustained release compositions of this invention comprise a biocompatible polymer, and agent, such as a biologically active polypeptide, and a sugar. The agent and sugar are dispersed in the biocompatible polymer separately or, preferably, together. In a particular embodiment, the sustained release composition is characterized by a release profile having a ratio of maximum serum concentration ($C_{max}$) to average serum concentration ($C_{ave}$) of about 3 or less. As used herein, the terms a or an refer to one or more.

The Agent

In a preferred embodiment, the agent is a biologically active polypeptide such as an antidiabetic or glucoregulatory polypeptide, including GLP-1, exendin-3, exendin-4 or an analog, derivative or agonist thereof. Most specifically, the polypeptide is exendin-4. However, other agents can take advantage of the discoveries made herein.

Biologically active polypeptides as used herein collectively refers to biologically active proteins and peptides and the pharmaceutically acceptable salts thereof, which are in their molecular, biologically active form when released in vivo, thereby possessing the desired therapeutic, prophylactic and/or diagnostic properties in vivo. Typically, the polypeptide has a molecular weight between 500 and 200,000 Daltons.

Suitable biologically active polypeptides include, but are not limited to, glucagon, glucagon-like peptides such as, GLP-1, GLP-2 or other GLP analogs, derivatives or agonists of Glucagon Like Peptides, exendins such as, exendin-3 and exendin-4, derivatives, agonists and analogs thereof, vasoactive intestinal peptide (VIP), immunoglobulins, antibodies, cytokines (e.g., lymphokines, monokines, chemokines), interleukins, macrophage activating factors, interferons, erythropoietin, nucleases, tumor necrosis factor, colony stimulating factors (e.g., G-CSF), insulin, enzymes (e.g., superoxide dismutase, plasminogen activator, etc.), tumor suppressors, blood proteins, hormones and hormone analogs and agonists (e.g., follicle stimulating hormone, growth hormone, adrenocorticotropic hormone, and luteinizing hormone releasing hormone (LHRH)), vaccines (e.g., tumoral, bacterial and viral antigens), antigens, blood coagulation factors, growth factors (NGF and EGF), gastrin, GRH, antibacterial peptides such as defensin, enkephalins, bradykinins, calcitonin and muteins, analogs, truncation, deletion and substitution variants and pharmaceutically acceptable salts of all the foregoing.

Exendin-4 is a 39 amino acid polypeptide. The amino acid sequence of exendin-4 can be found in U.S. Pat. No. 5,424,286 issued to Eng on Jun. 13, 1995, the entire content of which is hereby incorporated by reference. AC2993 and exenatide are synonymous with the term exendin-4. Exendin-4 has been shown in humans and animals to stimulate secretion of insulin in the presence of elevated blood glucose concentrations, but not during periods of low blood glucose concentrations (hypoglycemia). It has also been shown to suppress glucagon secretion, slow gastric emptying and affect food intake and body weight, as well as other actions. As such, exendin-4 and analogs and agonists thereof can be useful in the treatment of diabetes mellitus, IGT, obesity, etc.

The amount of biologically active polypeptide, which is contained within the polymeric matrix of a sustained release composition, is a therapeutically, diagnostically or prophylactically effective amount which can be determined by a person of ordinary skill in the art, taking into consideration factors such as body weight, condition to be treated, type of polymer used, and release rate from the polymer.

Sustained release compositions generally contain from about 0.01% (w/w) to about 50% (w/w) of the agent, e.g., biologically active polypeptide (such as exendin-4) (total weight of composition). For example, the amount of biologically active polypeptide (such as exendin-4) can be from about 0.1% (w/w) to about 30% (w/w) of the total weight of the composition. The amount of polypeptide will vary depending upon the desired effect, potency of the agent, the planned release levels, and the time span over which the polypeptide will be released. Preferably, the range of loading is between about 0.1% (w/w) to about 10% (w/w), for example, 0.5% (w/w) to about 5% (w/w). Superior release profiles were obtained when the agent, e.g. exendin-4, was loaded at about 3% w/w.

The Sugar

A sugar, as defined herein, is a monosaccharide, disaccharide or oligosaccharide (from about 3 to about 10 monosaccharides) or a derivative thereof. For example, sugar alcohols of monosaccharides are suitable derivatives included in the present definition of sugar. As such, the sugar alcohol mannitol, for example, which is derived from the monosaccharide mannose is included in the definition of sugar as used herein.

Suitable monosaccharides include, but are not limited to, glucose, fructose and mannose. A disaccharide, as further defined herein, is a compound which upon hydrolysis yields two molecules of a monosaccharide. Suitable disaccharides include, but are not limited to, sucrose, lactose and trehalose. Suitable oligosaccharides include, but are not limited to, raffinose and acarbose.

The amount of sugar present in the sustained release composition can range from about 0.01% (w/w) to about 50% (w/w), such as from about 0.01% (w/w) to about 10% (w/w), such as from about 0.1% (w/w) to about 5% (w/w) of the total weight of the sustained release composition. Excellent release profiles were obtained incorporating about 2% (w/w) sucrose.

Alternatively, the amount of sugar present in the sustained release composition can be referred to on a weight ratio with the agent or biologically active polypeptide. For example, the polypeptide and sugar can be present in a ratio from about 10:1 to about 1:10 weight:weight. In a particularly preferred embodiment, the ratio of polypeptide (e.g., exendin-4) to sugar (e.g., sucrose) is about 3:2 (w/w).

Combinations of two or more sugars can also be used. The amount of sugar, when a combination is employed, is the same as the ranges recited above.

When the polypeptide is exendin-4, the sugar is preferably sucrose, mannitol or a combination thereof.

The Polymer

Polymers suitable to form the sustained release composition of this invention are biocompatible polymers which can be either biodegradable or non-biodegradable polymers or blends or copolymers thereof. A polymer is biocompatible if the polymer and any degradation products of the polymer are non-toxic to the recipient and also possess no significant deleterious or untoward effects on the recipient's body, such as a substantial immunological reaction at the injection site.

Biodegradable, as defined herein, means the composition will degrade or erode in vivo to form smaller units or chemical species. Degradation can result, for example, by enzymatic, chemical and physical processes. Suitable biocompatible, biodegradable polymers include, for example, poly(lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or polyethylene glycol and polyorthoester, biodegradable polyurethane, blends thereof, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl fluoride, poly(vinyl imidazole), chlorosulphonate polyolefins, polyethylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, end group chemistry and rate of dissolution of polymer in solvent. Typically, an acceptable range of molecular weight is of about 2,000 Daltons to about 2,000,000 Daltons. In a preferred embodiment, the polymer is biodegradable polymer or copolymer. In a more preferred embodiment, the polymer is a poly(lactide-co-glycolide) (hereinafter "PLG") with a lactide:glycolide ratio of about 1:1 and a molecular weight of about 10,000 Daltons to about 90,000 Daltons. In an even more preferred embodiment, the molecular weight of the PLG used in the present invention has a molecular weight of about 30,000 Daltons to about 70,000 Daltons such as about 50,000 to about 60,000 Daltons.

The PLGs can possess acid end groups or blocked end groups, such as can be obtained by esterifying the acid. Excellent results were obtained with a PLG with an acid end group.

Polymers can also be selected based upon the polymer's inherent viscosity. Suitable inherent viscosities include about 0.06 to 1.0 dL/g, such as about 0.2 to 0.6 dL/g, more preferably between about 0.3 to 0.5 dL/g. Preferred polymers are chosen that will degrade in 3 to 4 weeks. Suitable polymers can be purchased from Alkermes, Inc. under the tradename Medisorb®, such as those sold as 5050 DL 3A or 5050 DL 4A. Boehringer Ingelheim Resomer® PLGs may also be used, such as Resomer® RG503 and 503H.

The sustained release composition of this invention can be formed into many shapes such as a film, a pellet, a cylinder, a disc or a microparticle. A microparticle, as defined herein, comprises a polymer component having a diameter of less than about one millimeter and having biologically active polypeptide dispersed or dissolved therein. A microparticle can have a spherical, non-spherical or irregular shape. Typically, the microparticle will be of a size suitable for injection. A typical size range for microparticles is 1000 microns or less. In a particular embodiment, the microparticle ranges from about one to about 180 microns in diameter.

Additional Excipients

While it is possible that additional excipients can be added to the formulations of the claimed invention as is well known in the art, a surprising discovery of the present invention is that an excellent release profile can be achieved with the simple formulation described herein. Such additional excipients can increase or decrease the rate of release of the agent. Ingredients which can substantially increase the rate of release include pore forming agents and excipients which facilitate polymer degradation. For example, the rate of polymer hydrolysis is increased in non-neutral pH. Therefore, an acidic or a basic excipient such as an inorganic acid or inorganic base can be added to the polymer solution, used to form the microparticles, to alter the polymer erosion rate. Ingredients which can substantially decrease the rate of release include excipients that decrease the water solubility of the agent.

A preferred embodiment of the described sustained release formulations consists essentially of the biocompatible polymer, the agent and the sugar. By "consists essentially of" is meant the absence of ingredients which substantially increase the rate of release of the active agent from the formulation. Examples of additional excipients which would not be expected to substantially increase or decrease the rate of release of the agent include additional active agents and inert ingredients.

In yet another embodiment, the formulation consists of the biocompatible polymer, the agent and the sugar. By "consists of" is meant the absence of components or ingredients other than those listed and residual levels of starting materials, solvents, etc. from the process.

It has been a surprising discovery that buffering agents such as acetate, citrate, phosphate or other biologically compatible buffer was not necessary in the aqueous phase to achieve a sustained release formulation with agent, e.g., exendin-4, with good to excellent bioavailability. It was also a surprising discovery that salting out salts were unnecessary to control burst of the agent, e.g., exendin-4. As such, the compositions of the invention also include compositions, as described herein, in the substantial (or complete) absence of buffer and/or salting out salts.

Alternatively or additionally, the sustained release composition of the invention has low porosity. In such embodiments, the sustained release composition comprises a biocompatible polymer, a biologically active polypeptide and a sugar wherein the composition has a total pore volume of about 0.1 mL/g or less. In a specific embodiment, the total pore volume is determined using mercury intrusion porosimetry, e.g., as described in more detail below.

Administration

The compositions of the invention can be administered according to methods generally known in the art. The composition of this invention can be administered to a patient (e.g., a human in need of the agent) or other animal, by injection, implantation (e.g., subcutaneously, intramuscularly, intraperitoneally, intracranially, and intradermally), administration to mucosal membranes (e.g., intranasally, intravaginally, intrapulmonary or by means of a suppository), or in situ delivery (e.g., by enema or aerosol spray).

The sustained release composition can be administered using any dosing schedule which achieves the desired therapeutic levels for the desired period of time. For example, the sustained release composition can be administered and the patient monitored until levels of the drug being delivered return to baseline. Following a return to baseline, the sustained release composition can be administered again. Alternatively, the subsequent administration of the sustained release composition can occur prior to achieving baseline levels in the patient.

For example, when the sustained release composition has incorporated therein a hormone, particularly an anti-diabetic or glucoregulatory peptide, for example, GLP-1, GLP-2, exendin-3, exendin-4 or agonists, analogs or derivatives thereof, the composition is administered in a therapeutically effective amount to treat a patient suffering from diabetes mellitus, IGT, obesity, cardiovascular (CV) disorder or any other disorder that can be treated by one of the above polypeptides or derivatives, analogs or agonists thereof.

Other conditions which can be treated by administering the sustained release composition of the invention include Type I and Type II diabetes which can be treated with a sustained release composition having insulin incorporated therein. In addition, when the incorporated polypeptide is FSH or analogs thereof the sustained release composition can be used to treat infertility. In other instances, the sustained release composition can be used to treat Multiple Sclerosis when the incorporated polypeptide is beta interferon or a mutein thereof. As can be realized, the sustained release composition can be used to treat disease which responds to administration of a given polypeptide.

In a further embodiment, the sustained release composition of the present invention can be coadministered with a corticosteroid. Coadministration of the sustained release composition of the invention with a corticosteroid can further increase the bioavailability of the biologically active polypeptide of the sustained release composition. Coadministration of a corticosteroid in combination with sustained release compositions is described in detail in U.S. Patent Application 60/419,430 entitled, "Method of Modifying the Release Profile of Sustained Release Compositions" by Dasch et al. the entire content of which is hereby incorporated by reference.

Corticosteroids, as defined herein, refers to steroidal anti-inflammatory agents also referred to as glucocorticoids.

Suitable corticosteroids include, but are not limited to, 21-Acetoxypregnenolone, Alclometasone, Algestone, Amcinonide, Beclomethasone, Betamethasone, Budesonide, Chloroprednisone, Clobetasol, Clobetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumethasone, Flunisolide, Flucinolone Acetonide, Fluocinonide, Fluocortin Butyl, Flucortolone, Fluorometholone, Fluperolone Acetate, Fluprednidene Acetate, Fluprednisolone, Flurandrenolide, Fluticasone Propionate, Formocortal, Halcinonide, Halobetasol Propionate, Halometasone, Halopredone Acetate, Hydrocortamate, Hydrocortisone, Loteprednol Etabonate, Mazipredone, Medrysone, Meprednisone, Methylprednisolone, Mometasone Furoate, Paramethasone, Prednicarbate, Prednisolone, Prednisolone 25-Diethylamino-acetate, Prednisolone Sodium Phosphate, Prednisone, Prednival, Prednylidene, Rimexolone, Tixocortol, Triamcinolone (all forms), for example, Triamcinolone Acetonide, Triamcinolone Acetonide 21-oic acid methyl ester, Triamcinolone Benetonide, Triamcinolone Hexacetonide, Triamcinolone Diacetate, pharmaceutically acceptable mixtures thereof and salts thereof and any other derivative and analog thereof.

In one embodiment, the corticosteroid can be co-incorporated into the sustained release composition comprising the biocompatible polymer and the biologically active polypeptide agent incorporated therein.

In another embodiment, the corticosteroid can be separately incorporated into a second biocompatible polymer. The second biocompatible polymer can be the same or different from the first biocompatible polymer which has the biologically active polypeptide agent incorporated therein.

In yet another embodiment, the corticosteroid can be present in an unencapsulated state but commingled with the sustained release composition. For example, the corticosteroid can be solubilized in the vehicle used to deliver the sustained release composition. Alternatively, the corticosteroid can be present as a solid suspended in an appropriate vehicle. Further, the corticosteroid can be present as a powder which is commingled with the sustained release composition.

It is understood that the corticosteroid is present in an amount sufficient to increase the bioavailability of the biologically active polypeptide from the sustained release composition. Increased bioavailability refers to an increase in the bioavailability of the biologically active polypeptide from the sustained release composition when co-administered with a corticosteroid in comparison to the administration in the absence of corticosteroid over a time period beginning at two days post administration and ending at the end of the release cycle for the particular formulation.

As used herein, patient refers to a human, such as a human in need of the agent or therapy, prophylaxis or diagnostic method.

As defined herein, a sustained release of biologically active polypeptide is a release of the polypeptide from the sustained release composition of the invention which occurs over a period which is longer than that period during which a biologically significant amount of the polypeptide would be available following direct administration of a solution of the polypeptide. It is preferred that a sustained release be a release which occurs over a period of at least about one week, such as at least about two weeks, at least about three weeks or at least about four weeks. The sustained release can be a continuous or a discontinuous release, with relatively constant or varying rates of release. The continuity of release and level of release can be affected by the type of polymer composition used (e.g., monomer ratios, molecular weight, block composition, and varying combinations of polymers), polypeptide loading, and/or selection of excipients to produce the desired effect.

As used herein, a therapeutically effective amount, prophylactically effective amount or diagnostically effective amount is the amount of the sustained release composition needed to elicit the desired biological response following administration.

$C_{max}$ as used herein is the maximum serum concentration of drug which occurs during the period of release which is monitored.

$C_{ave}$ as used herein, is the average serum concentration of drug derived by dividing the area under the curve (AUC) of the release profile by the duration of the release.

It is preferred that the ratio of $C_{max}$ to $C_{ave}$ be about 3 or less. This profile is particularly desirable of anti-diabetic or glucoregulatory polypeptides, such as those described above. A ratio of about 3 or less can provide a $C_{ave}$ in a therapeutic window while avoiding adverse drug side effects which can result from higher ratios.

Bioavailability, as that term is used herein, refers to the amount of therapeutic that reaches the circulation system. Bioavailability can be defined as the calculated Area Under the Curve (AUC) for the release profile of a particular polypeptide during the time period starting at post administration and ending at a predetermined time point. As is understood in the art, the release profile is generated by graphing the serum levels of a biologically active agent in a subject (Y-axis) at predetermined time points (X-axis). Bioavailability is often referred to in terms of % bioavailability, which is the bioavailability achieved for a particular polypeptide following administration of a sustained release composition divided by the bioavailability achieved for a particular polypeptide following intravenous administration of the same dose of drug, multiplied by 100.

A modification of the release profile can be confirmed by appropriate pharmacokinetic monitoring of the patient's serum for the presence of the biologically active polypeptide agent. For example, specific antibody-based testing (e.g., ELISA and IRMA), as is well known in the art, can be used to determine the concentration of certain biologically active polypeptide agents in the patient's serum. An example of such testing is described herein for exendin-4.

Pharmacodynamic monitoring of the patient to monitor the therapeutic effects of the agent upon the patient can be used to confirm retention of the biological activity of the released agent. Methods of monitoring pharmacodynamic effects can be selected based upon the biologically active polypeptide agent being administered using widely available techniques.

Manufacture

A number of methods are known by which sustained release compositions (polymer/biologically active polypeptide matrices) of the invention can be formed, particularly compositions having low porosity as described herein. Detailed procedures for some methods of microparticle formation are set forth in the Working Examples. In a preferred embodiment, the method of the invention for forming a composition for the sustained release of biologically active polypeptide includes forming a mixture by combining an aqueous phase comprising water, agent, such as a water soluble polypeptide, and a sugar with an oil phase comprising a biocompatible polymer and a solvent for the polymer; forming a water-in-oil emulsion; adding a coacervation agent, for example silicone oil, vegetable oil or mineral oil to the mixture to form embryonic microparticles; transferring the embryonic microparticles to a quench solvent to harden the microparticles; collecting the hardened microparticles; and drying the hardened microparticles. This process is generally referred to herein as a water-oil-oil process (W/O/O).

Preferably, the polymer can be present in the oil phase in a concentration ranging from about 3% w/w to about 25% w/w, preferably, from about 4% w/w to about 15% w/w, such as from about 5% w/w to about 10% w/w. Excellent results were obtained herein using a 6% w/w concentration of PLG in the oil phase.

The polymer is generally combined with a polymer solvent. Where the polymer is a PLG, such as those preferred herein, the polymer is added to a solvent for PLG. Such solvents are well known in the art. A preferred solvent is methylene chloride.

The agent and sugar are added in the aqueous phase, preferably in the same aqueous phase. The concentration of agent is preferably 10 to 100 mg/g, preferably between 50 to 100 mg/g. The concentration of sugar is preferably 10 to 50 mg/g and 30 to 50 mg/g.

The two phases are then mixed to form an emulsion. It is preferred that the emulsion be formed such that the inner emulsion droplet size is less than about 1 micron, preferably less than about 0.7 microns, more preferably less than about 0.5 microns, such as about 0.4 microns. Sonicators and homogenizers can be used to form such an emulsion.

A coacervation agent as used herein refers to any oil in which the polymer solution (polymer and solvent) is not readily solubilized into and thereby forms a distinct phase with the polymer solution. Suitable coacervation agents for use in the present invention include, but are not limited to, silicone oil, vegetable oil and mineral oil. In a particular embodiment, the coacervation agent is silicone oil and is added in an amount sufficient to achieve a silicone oil to polymer solvent ratio from about 0.75:1 to about 2:1. In a particular embodiment, the ratio of silicone oil to polymer is from about 1:1 to about 1.5:1. In a preferred embodiment, the ratio of silicone oil to polymer is about 1.5:1.

The resulting mixture is added to a quench, which comprises a polymer non-solvent. Polymer non-solvents are generally well known in the art. A particularly preferred quench comprises a heptane/ethanol solvent system.

Solid drug can also be encapsulated using a modified version of the process described above. This modified process can be referred to as a solid/oil/oil (S/O/O).

For example, solid exendin-4 was suspended in methylene chloride containing 6% PLG and sonicated for about four minutes on ice. Subsequent processing was conducted in a manner analogous to the W/O/O method.

The invention will now be further and specifically described by the following examples.

EXEMPLIFICATIONS

Microparticle Preparation I

The sustained release compositions described herein were prepared by a phase separation process. The general process is described below for microparticles containing exendin-4 and sucrose for a 1 kg batch size.

A. Inner Water-in-Oil Emulsion Formation

A water-in-oil emulsion was created with the aid of a homogenizer. Suitable homogenizers include an in-line Megatron homogenizer MT-V 3-65 F/FF/FF, Kinematica AG, Switzerland. The water phase of the emulsion was prepared by dissolving exendin-4 and excipients such as sucrose in water. The concentration of drug in the resulting solution can be from about 50 mg/g to about 100 mg/g. For example, when the drug is exendin-4, the concentration of drug in solution can be from about 30 g to about 60 g per 600 g of water. In a particular embodiment, 50 g exendin-4 and 20 g sucrose were dissolved in 600 g water for irrigation (WFI). The specified amounts listed above represent a nominal load without adjustment to compensate for peptide content strength specific to the lot of exendin-4 used. The oil phase of the emulsion was prepared by dissolving PLGA polymer (e.g., 930 g of purified 50:50 DL4A PLGA (Alkermes, Inc.) in methylene chloride (14.6 kg or 6% w/w).

The water phase was then added to the oil phase to form a coarse emulsion with an overhead mixer for about three minutes. Then, the coarse emulsion was homogenized at approximately 10,000 rpm at ambient temperature. This resulted in an inner emulsion droplet size of less than 1 micron. It is understood that inner emulsion formation can be achieved using any suitable means. Suitable means of emulsion formation include, but are not limited to, homogenization as described above and sonication.

B. Coacervate Formation

A coacervation step was then performed by adding silicone oil (21.8 kg of Dimethicone, NF, 350 cs) over about a five minute time period to the inner emulsion. This is equivalent to a ratio of 1.5:1, silicone oil to methylene chloride. The methylene chloride from the polymer solution partitions into the silicone oil and begins to precipitate the polymer around the water phase containing exendin-4, leading to microencapsulation. The embryonic microspheres thus formed are soft and require hardening. Frequently, the embryonic microspheres are permitted to stand for a short period of time, for example, from about 1 minute to about 5 minutes prior to proceeding to the microsphere hardening step.

C. Microsphere Hardening and Rinse

The embryonic microspheres were then immediately transferred into a heptane/ethanol solvent mixture. The volume of heptane/ethanol mixture needed can be determined based on the microsphere batch size, typically a 16:1 ratio of methylene chloride to heptane/ethanol solvent. In the present example, about 210 kg heptane and 23 kg ethanol in a 3° C. cooled, stirred tank were used. This solvent mixture hardened the microspheres by extracting additional methylene chloride from the microspheres. This hardening step can also be referred to as quenching. After being quenched for 1 hour at 3° C., the solvent mixture is either decanted and fresh heptane (13 Kg) is added at 3° C. and held for 1 hour to rinse off residual silicone oil, ethanol and methylene chloride on the microsphere surface or pumped directly to the collection step.

D. Microsphere Drying and Collection

At the end of the quench or decant/wash step, the microspheres were transferred and collected on a 12" Sweco Pharmasep Filter/Dryer Model PH12Y6. The filter/dryer uses a 20 micron multilayered collection screen and is connected to a motor that vibrates the screen during collection and drying. A final rinse with heptane (6 Kg at 3° C.) was performed to ensure maximum line transfer and to remove any excess silicone oil. The microspheres were then dried under vacuum with a constant purge of nitrogen gas at a controlled rate according to the following schedule: 6 hours at 3° C.; 6 hours ramping to 41° C.; and 84 hours at 41° C.

After the completion of drying, the microspheres were discharged into a collection vessel, sieved through a 150 μm sieve, and stored at about −20° C. until filling.

For all microparticle formulations which were prepared herein the amount of polypeptide, for example, exendin-4 and excipients present in the prepared formulations is expressed as a % (w/w) based on the final weight of the sustained release composition. The % (w/w) is a nominal percentage, except where indicated.

Microparticle Preparation II

A. Inner Water-in-Oil Emulsion Formation

A water-in-oil emulsion was created with the aid of a sonicator. Suitable sonicators include Vibracell VCX 750 with model CV33 probe head, Sonics and Materials Inc., Newtown, Conn. The water phase of the emulsion was prepared by dissolving exendin-4 and excipients such as sucrose in water. The concentration of drug in the resulting solution can be from about 50 mg/ml to about 100 mg/ml. For example, when the drug is exendin-4, the concentration of drug in solution can be from about 3.28 g to about 6.55 g per 65.5 g of water. In a particular embodiment, 5.46 g exendin-4 and 2.18 g sucrose were dissolved in 65.5 g water for irrigation or WFI. The specified amounts listed above represent a 4% overage to target load in order to compensate for losses upon filter sterilization of the components. The oil phase of the emulsion was prepared by dissolving PLGA polymer (e.g., 97.7 g of purified 50:50 DL4A PLGA (Alkenes, Inc.)) in methylene chloride (1539 g or 6% w/v).

The water phase was then added to the oil phase over about a three minute period while sonicating at 100% amplitude at ambient temperature. The water phase was pumped through a ¼" stainless steel tube with a 1" HPLC tube end (ID=20/1000") at 5 psig, added below the sonication probe inside the sonication zone. Reactor was then stirred at 1400 to 1600 rpm, with additional sonication at 100% amplitude for 2 minutes, followed by a 30 second hold, and then 1 minute more of sonication. This resulted in an inner emulsion droplet size of less than 0.5 microns. It is understood that inner emulsion formation can be achieved using any suitable means. Suitable means of emulsion formation include, but are not limited to, sonication as described above and homogenization.

B. Coacervate Formation

A coacervation step was then performed by adding silicone oil (2294 gr of Dimethicone, NF, 350 cs) over about a three to five minute time period to the inner emulsion. This is equivalent to a ratio of 1.5:1, silicone oil to methylene chloride. The methylene chloride from the polymer solution partitions into the silicone oil and begins to precipitate the polymer around the water phase containing exendin-4, leading to microencapsulation. The embryonic microspheres thus formed are soft and require hardening. Frequently, the embryonic microspheres are permitted to stand for a short period of time, for example, from about 1 minute to about 5 minutes prior to proceeding to the microsphere hardening step.

C. Microsphere Hardening and Rinse

The embryonic microspheres were then immediately transferred into a heptane/ethanol solvent mixture. The volume of heptane/ethanol mixture needed can be determined based on the microsphere batch size. In the present example, about 22 kg heptane and 2448 g ethanol in a 3° C. cooled, stirred tank (350 to 450 rpm) were used. This solvent mixture hardened the microspheres by extracting additional methylene chloride from the microspheres. This hardening step can also be referred to as quenching. After being quenched for 1 hour at 3° C., the solvent mixture was decanted and fresh heptane (13 Kg) was added at 3° C. and held for 1 hour to rinse off residual silicone oil, ethanol and methylene chloride on the microsphere surface.

D. Microsphere Drying and Collection

At the end of the rinse step, the microspheres were transferred and collected on a 6" diameter, 20 micron multilayered screen inside the cone shaped drying chamber which acted as a dead-end filter. A final rinse with heptane (6 Kg at 4° C.) was performed to ensure maximum line transfer. The microspheres were then dried with a constant purge of nitrogen gas at a controlled rate according to the following schedule: 18 hours at 3° C.; 24 hours at 25° C.; 6 hours at 35° C.; and 42 hours at 38° C.

After the completion of drying, the microspheres are discharged into a teflon/stainless steel sterilized collection vessel attached to the drying cone. The collection vessel is sealed, removed from the drying cone and stored at −20±5° C. until filling. Material remaining in the cone upon disassembly for cleaning is taken for drug content analysis. The yield was approximately 100 grams of microspheres.

For all microparticle formulations which were prepared herein the amount of polypeptide, for example, exendin-4 and excipients present in the prepared formulations is expressed as a % (w/w) based on the final weight of the sustained release composition. The % (w/w) is a nominal percentage, except were indicated.

Polymer:

Examples of specific PLG polymers suitable for use are listed below. All of the polymers employed in the following examples are set forth in the list and all listed polymers were obtained from Alkermes, Inc. of Cincinnati, Ohio and can be described as follows:

Polymer 2A: Poly(lactide-co-glycolide); 50:50 lactide:glycolide ratio; 12.3 kD Mol. Wt.; IV=0.15 (dL/g).

Polymer 4A: Poly(lactide-co-glycolide); 50:50 lactide:glycolide ratio; Mol. Wt. 45-64 kD; I=0.45-0.47 (dL/g).

PURIFICATION OF PLG: It is known in the art (See, for example, Peptide Acylation by Poly(α-Hydroxy Esters) by Lucke et al., Pharmaceutical Research, Vol. 19, No. 2, p. 175-181, February 2002) that proteins and peptides which are incorporated in PLG matrices can be undesirably altered (e.g., degraded or chemically modified) as a result of interaction with degradation products of the PLG or impurities remaining after preparation of the polymer. As such, the PLG polymers used in the preparation of the majority of microparticle formulations described herein were purified prior to preparation of the sustained release compositions using art recognized purification methods.

Characterization Methods:

It has been determined that the following characterization methods are suitable for identifying microparticles which will provide a desirable release profile of active agent.

SEM

SEM was used to assess the particle size, shape and surface features of the microparticles. SEM imaging was performed on a Personal SEM® system (ASPEX™, LLC). All samples were deposited via spatula on standard SEM stubs covered with carbon double-sided tape. Samples were sputter coated with Au for about 90 seconds at 18 mA emission current using a Model SC 7620 "Mini" Sputter Coater (Energy Beam Sciences). All SEM imaging was performed utilizing a 20 KeV electron beam over a magnification range of approximately 250 to 2500×.

Cryogenic SEM

The cross-section of microparticles was studied using cryogenic SEM. The microparticle sample was mixed with HISTO PREP® Solution (Fischer) and kept in a cryostat at −20° C. overnight. The hardened microparticles were mounted on a glass cover slip and then sectioned using a metal knife. The sectioned particles were mounted on aluminium stubs, sputter coated with Platinum and Palladium and observed under a Scanning Electron Microscope (Phillips 525M). Visual observation of the sections provides a method of determining the degree of porosity for the microparticles.

Porosity Measurement-Mercury Intrusion

Pore volume distribution in microparticles was determined using a model SutoPor IV 9500 Moden Mercury Intrusion Porosimeter (Micromeritics, Norcross, Ga.). Briefly, mercury was forced into a known amount of microparticles in a penetrometer by applying pressure in a step-wise manner up to a maximum pressure of 60,000 Psia. The volume of mercury intruded into the pores at various pressures was measured. This method quantifies the pore distribution in the microparticles. That is, the size of the pores that are intruded is inversely related to the applied pressure. The equilibrium of the internal and external forces on the liquid-solid-vapor system can be described by the Washburn equation. The relationship between applied pressure and the pore size into which mercury is forced to enter is described by:

$$D = -\frac{4\gamma\cos\theta}{P}$$

Where:
D=pore diameter
γ=surface tension (constant)
θ=contact angle (constant)
P=Pressure Therefore, the size of the pore into which mercury will intrude is inversely proportional to the applied pressure. Assuming that all pores are tight cylinders, the average pore diameter (D=4V/A) can be calculated by dividing pore volume (V=πD2h/4) by the pore area (A=πDh).

Residual Solvents

A single method was used for quantitation of heptane, ethanol and methylene chloride. The equipment consisted of an HP 5890 Series 2 gas chromatograph with an Rtx 1301, 30 cm×0.53 mm column. About 130 mg microparticles were dissolved in 10 ml N,N-dimethylformamide. Propyl acetate was used as the internal standard. The sample preparation was adjusted so that concentrations of methylene chloride as low as 0.03% can be quantitated.

Microparticle Preparation

The microparticle batches set forth in Table 1 were prepared as described above at the 100 gram scale using the 4A polymer and a ratio of silicone oil to methylene chloride of either 1.5:1 or 1:1 and the silicone oil had a viscosity of 350 cs. The amount of exendin-4 and the excipients used in the formulation are also set forth in Table 1.

TABLE 1

| Lot # | Formulation | In vitro burst (%) | Remarks |
| --- | --- | --- | --- |
| 02-019-147(#1) | 0% Sucrose, 0% AS | 0.40 | 1.5:1 Si Oil:MeCl$_2$ |
| 02-019-167(#2) | 2% Sucrose (F16) | 0.40 | 1.5:1 Si Oil:MeCl$_2$ |
| 02-019-160(#2-1) | 2% Sucrose (F16) | 0.44 | 1.5:1 Si Oil:MeCl$_2$ |
| 02-019-164(#2-2) | 2% Sucrose (F16) | 0.45 | 1.5:1 Si Oil:MeCl$_2$ |
| 02-030-08(#2-3) | 2% Sucrose (F16) | 0.80 | 1:1 Si Oil:MeCl$_2$ |
| 02-030-01(#2-4) | 2% Sucrose (F16) | 1.0 | 1:1 Si Oil:MeCl$_2$ |
| 02-030-04(#2-5) | 2% Sucrose (F16) | 1.1 | 1:1 Si Oil:MeCl$_2$ |
| 02-019-136(#3-1) | 2% Sucrose, 0.5% AS (F14) | 1.3 | 50:50 Quench |

TABLE 1-continued

| Lot # | Formulation | In vitro burst (%) | Remarks |
|---|---|---|---|
| 02-019-115(#3-2) | 2% Sucrose, 0.5% AS (F14) | 2.2 | 1.5:1 Si Oil:MeCl$_2$ |
| 02-019-170(#4) | 0% Sucrose, 0.5% AS | 3.8 | 1.5:1 Si Oil:MeCl$_2$ |
| 02-019-133A(#3-3) | 2% Sucrose, 0.5% AS (F14) | 12.7 | 100% Heptane Quench |
| 02-019-185(#5) (5% drug load) | 2% sucrose (F17) | 0.5 | 5% drug load, 1.5:1 Si Oil:MeCl$_2$ |
| 02-019-64(#3-4) | 2% Sucrose, 0.5% AS (F14) | 0.5 | 1.5:1 Si Oil:MeCl$_2$ |
| 02-019-10(#3-5) | 2% Sucrose, 0.5% AS (F14) | 1.30 | 1:1 Si Oil:MeCl$_2$ |
| 02-001-196(#3-6) | 2% Sucrose, 0.5% AS (F14) | 2.70 | 1:1 Si Oil:MeCl$_2$ |
| 02-019-24(#3-7) | 2% Sucrose, 0.5% AS (F14) | 6.70 | 1:1 Si Oil:MeCl$_2$ |

* ALL FORMULATIONS HAD 3% DRUG LOAD WITH THE EXCEPTION OF #5 POROSITY

The total intrusion volume obtained from the mercury intrusion porosimetry and the calculated average pore diameters are given in TABLE 2. The relationship between the average pore diameter and the in vitro release is shown in FIG. 1

TABLE 2

| Lot # | Total Pore Volume (mL/g) | In vitro burst (%) | Average Pore Diameter (μm) |
|---|---|---|---|
| 02-019-147(#1) | 0.033 | 0.40 | 0.0068 |
| 02-019-167(#2) | 0.035 | 0.40 | 0.0069 |
| 02-019-160(#2-1) | 0.037 | 0.44 | 0.0070 |
| 02-019-164(#2-2) | 0.035 | 0.45 | 0.0070 |
| 02-030-08(#2-3) | 0.036 | 0.80 | 0.0070 |
| 02-030-01(#2-4) | 0.038 | 1.0 | 0.0073 |
| 02-030-04(#2-5) | 0.039 | 1.1 | 0.0074 |
| 02-019-136(#3-1) | 0.041 | 1.3 | 0.0073 |
| 02-019-115(#3-2) | 0.039 | 2.2 | 0.0078 |
| 02-019-170(#4) | 0.067 | 3.8 | 0.0125 |
| 02-019-133A(#3-3) | 0.513 | 12.7 | 0.0277 |
| 02-019-64(#3-4) | 0.030 | 0.5 | 0.0060 |
| 02-019-10(#3-5) | 0.060 | 1.30 | 0.0090 |
| 02-001-196(#3-6) | 0.060 | 2.70 | 0.0100 |
| 02-019-24(#3-7) | 0.180 | 6.70 | 0.0170 |

FIG. 1 shows the effect of ammonium sulfate on the in vitro initial release. The data indicate that in vitro initial release is correlated to the microparticle pore diameter. Formulations made with ammonium sulfate showed varying levels of in vitro release and variable porosity unlike the formulations without ammonium sulfate which exhibited consistent porosity and release. During the manufacturing of microparticles the presence of ammonium sulfate in the aqueous phase can salt-out the drug substance during the preparation of the inner-emulsion. The differences in the micro-environment of the precipitates can contribute to the differences in porosity and hence the variation in the initial release. The effect was not observed in formulations prepared without ammonium sulfate. Formulations with sucrose and exendin-4 show a more desirable and consistent level of initial release as compared to formulations having exendin-4, sucrose and ammonium sulfate.

Figure 2:
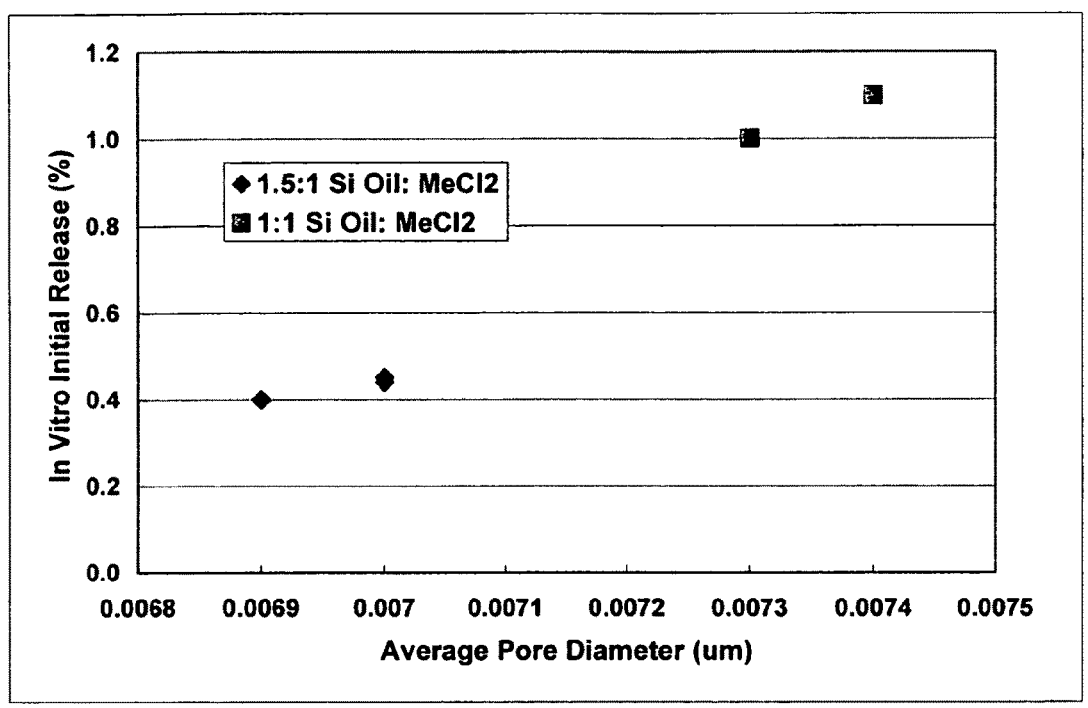
FIG. 2 is a graph showing the effect of porosity on the in vitro release of exendin-4 from microparticles and the impact that the processing conditions, namely the ratio of silicone oil to methylene chloride, has on the porosity of the microparticles formed.

FIG. 2 further demonstrates the effect of porosity on the in vitro release and the impact that the processing conditions, namely the ratio of silicone oil to methylene chloride, has on the porosity of the microparticles formed. Briefly, microparticle formulations prepared using a silicone oil-to-methylene chloride ratio of 1:1 (Formulations 2-4 and 2-5 of Table 1) have a higher initial release than the same formulations prepared using a silicone-to-methylene chloride ratio of 1.5:1 (Formulations 2, 2-1 and 2-2 of Table 1). FIG. 2 suggests that a higher ratio of silicone oil-to-methylene chloride results in a lower porosity which results in a lower initial release.

Cryogenic SEM

Figure 3B:
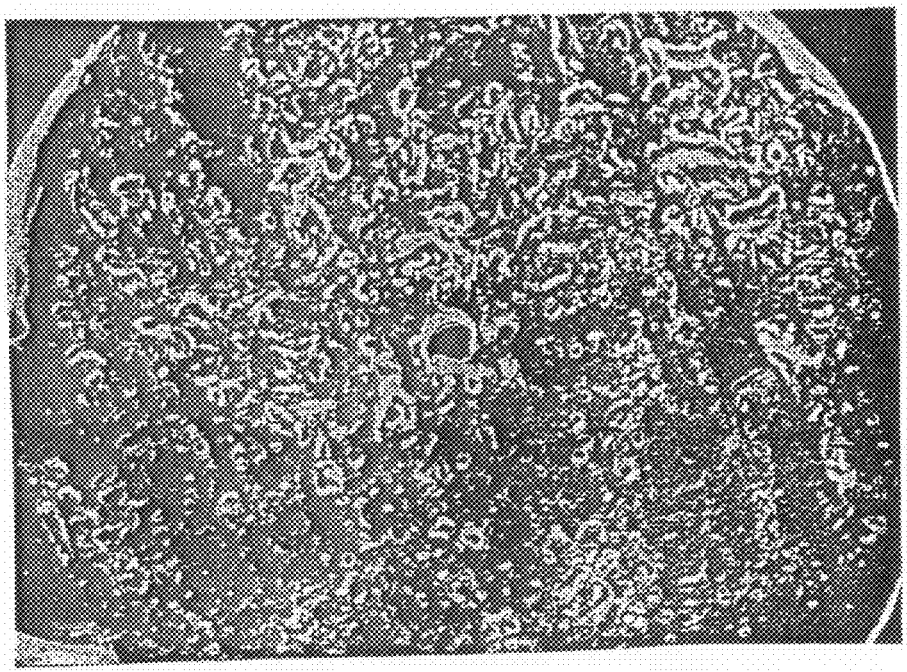
FIGS. 3A-3B are scans of cryogenic SEMs for selected microparticle formulations described herein.
Figure 3A:
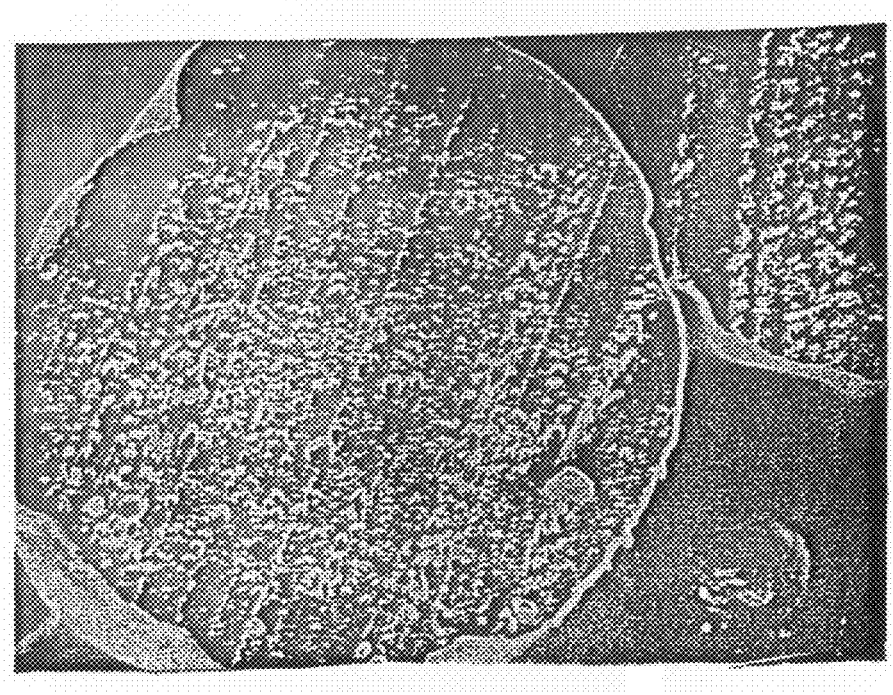
Figure 4B:
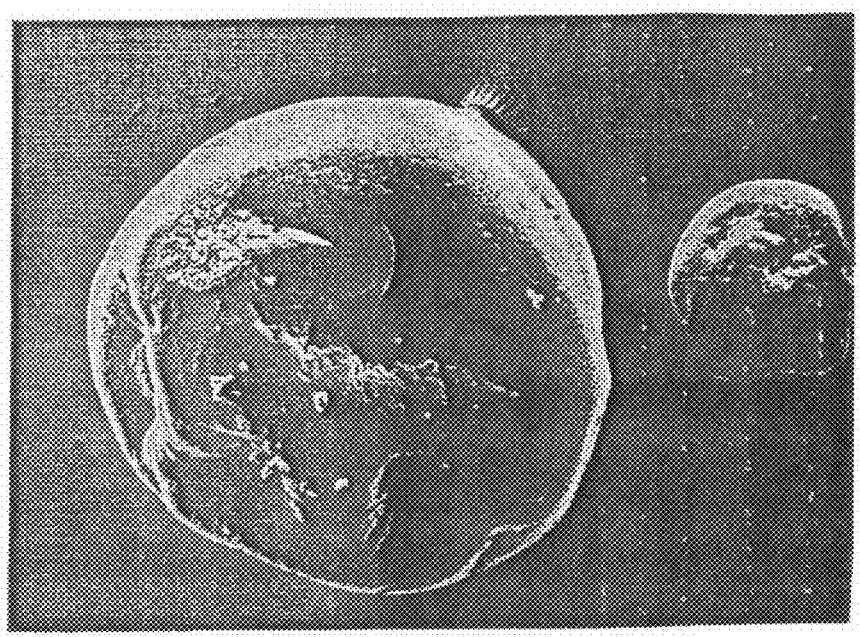
FIG. 4A-4D are scans of cryogenic SEMs for selected microparticle formulations described herein.
Figure 4A:
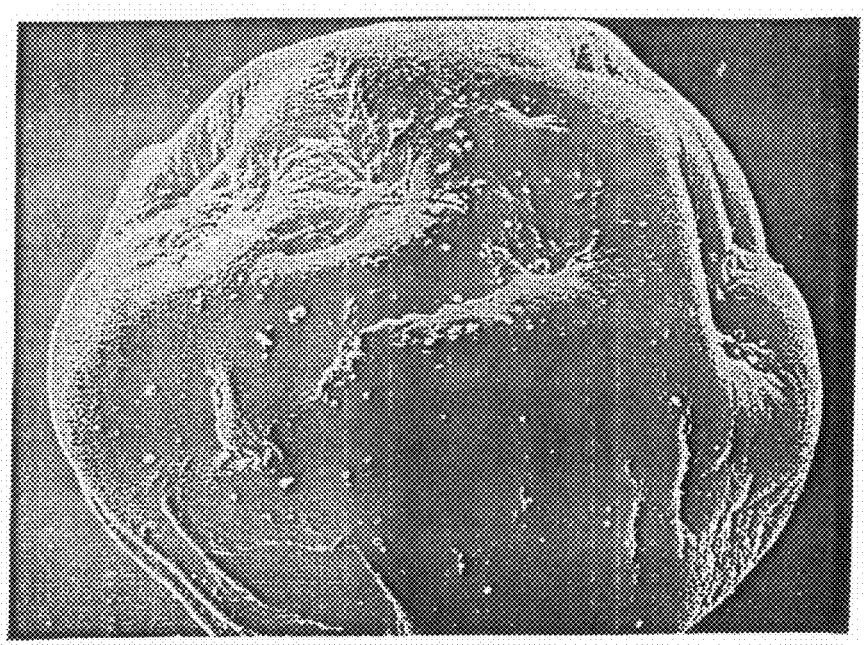
Figure 4D:
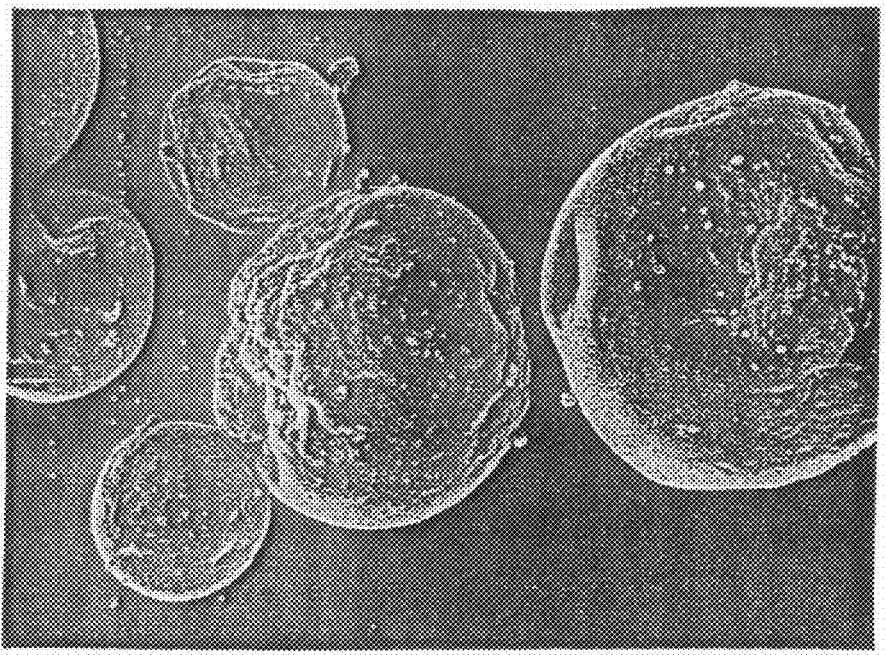
Figure 4C:
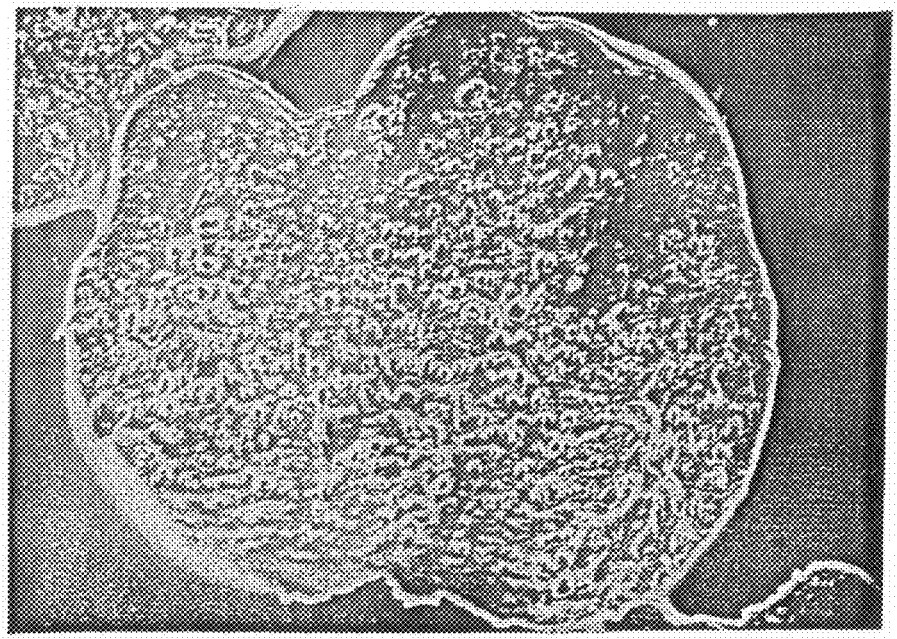

Cryogenic SEM analysis was conducted as described above on Formulations of the Types 2, 3 and 5 of Table 1. FIGS. 3A-3B are scans of micrographs for selected formulations of Type 2 (Formulation 2-2, FIG. 3A) and of Type 5 (5% exendin-4, 2% sucrose, FIG. 3B). FIGS. 4A-D are scans of micrographs for Formulations 3-4, 3-5, 3-6 and 3-7, respectively of Table 1. Again the variation in porosity exhibited with the use of ammonium sulfate which can contribute to the variability in initial release, can be seen in the cryogenic SEM cross sections of FIGS. 4A-D.

Residual Solvent Levels

The level of residual solvents in a given formulation can impact the Tg of the formulation. Residual solvent levels were determined for microparticle formulations of Types 2 and 5 of Table 1. A single method was used for quantitation of heptane, ethanol and methylene chloride. The equipment consisted of an HP 5890 Series 2 gas chromatograph with an Rtx 1301, 30 m×0.53 mm column. About 130 mg microparticles were dissolved in 10 ml N,N-dimethylformamide. Propyl acetate was used as the internal standard. The sample preparation was adjusted so that concentrations of methylene chloride as low as 0.03% can be quantitated.

Figure 5:
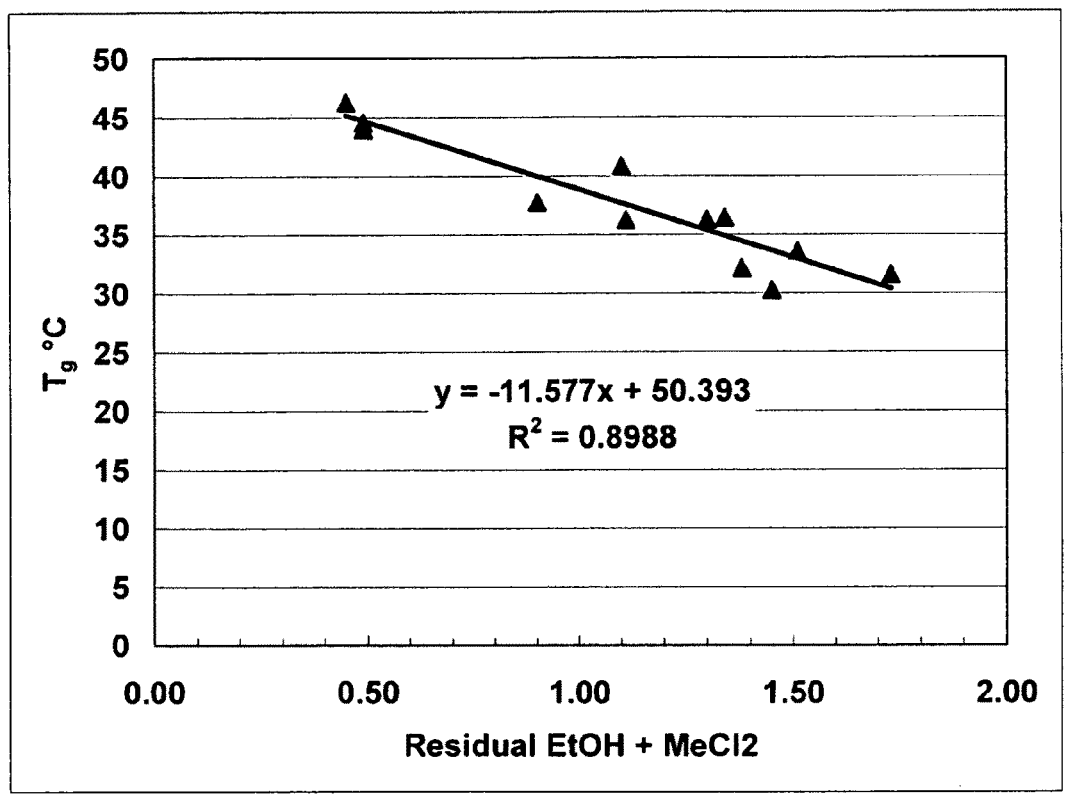
FIG. 5 is a plot of % residual ethanol and methylene chloride versus Tg for microparticle formulations described herein.

FIG. 5 is a plot of % residual ethanol and methylene chloride for formulations of Types 2 and 5 of Table 1 (3 or 5% exendin-4, 2% sucrose). FIG. 5 shows that the Tg decreases as the amount of residual solvent increases.

Preparation of Microparticles Having 3% Exendin-4 and 2% Sucrose

In view of the variation in porosity introduced by the presence of ammonium sulfate in the microparticle formulations and the identification of porosity as a characteristic which significantly impacts initial release, ammonium sulfate was not pursued in further discovery.

Impact of Inner Emulsion Droplet Size

The following study was done to determine the impact of process parameters on forming the inner emulsion as well as stability of the resulting emulsion and resulting 24 hour in vitro release of microspheres produced using the different process parameters. Inner emulsions of the water phase and solvent phase were formed by either sonication as described above for the 100 gr scale or homogenization using an MT5000 homogenizer with a 36/4 generator (Kinematica AG, Switzerland) at either a low speed (10,800 rpm) or high speed (21,300 rpm). Following inner emulsion formation by the different techniques, the emulsions were held in the reactor with gentle agitation with an overhead stirrer for 5, 15 or 60 minutes prior to an aliquot being removed. Following the designated hold times, the inner emulsion was further processed as described above into microparticles and then the 24 hour in vitro release determined for each batch as described below.

Figure 9:
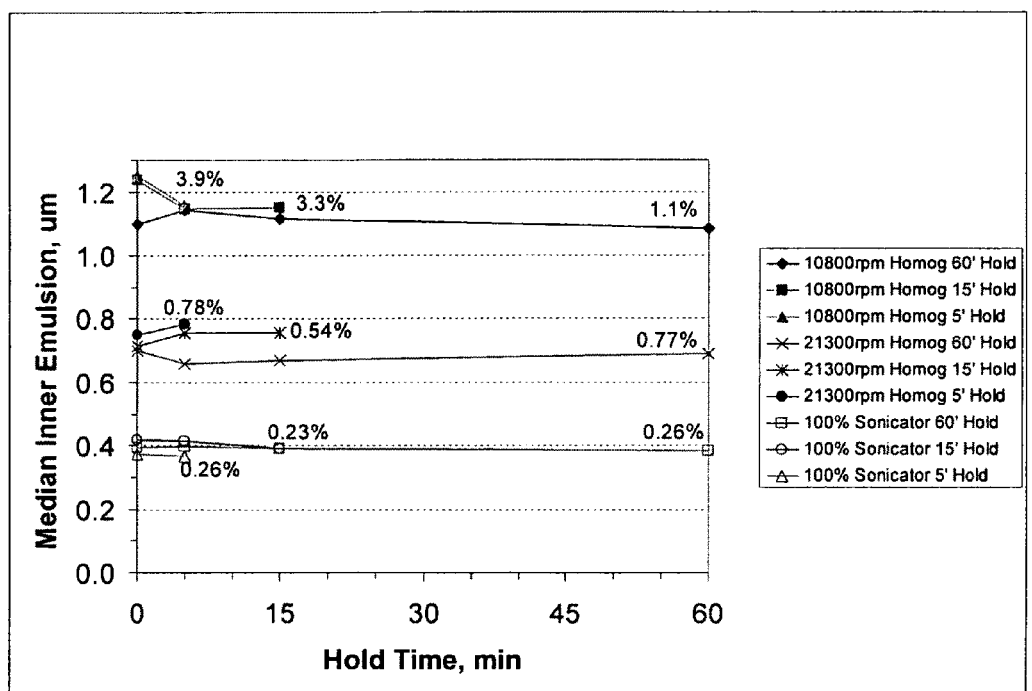
FIG. 9 is a graph illustrating the relationship between process parameters and the inner emulsion size achieved by the process.

Inner Emulsion Droplet Size Characterization can be Determined Using the Horiba Particle Size Analyzer An aliquot of the inner emulsion was withdrawn from the reactor using a glass pipet. Using a transfer pipet, ~30 drops of the inner emulsion was added to ~10 ml of 6% Medisorb® 50:50 4A PLG polymer solution in a 20 cc screw-cap scintillation vial followed by mixing. The 6% Medisorb® 50:50 4A PLG polymer solution also served as the reference blank solution. About 9 ml of this diluted emulsion sample was then transferred into a clean 10 ml Horiba sample holder. A cover was placed on the sample holder to prevent rapid evaporation of the polymer solvent. The prepared sample was within the acceptable % transmission reading range of 0.65%-0.90% per the blue bar (Lamp). A relative refractive index setting of 0.94-0.00i was selected in the program setup. The sample was then measured by a Horiba particle size analyzer such as model LA 910 for droplet size. The data correlating the process parameters and the achieved inner emulsion size over the 5, 15 and 60 minute hold times as well as the resulting 24 hour in vitro release results (in parenthesis) are shown in FIG. 9.

Microsphere Characterization

Exendin-4 microspheres were routinely characterized with respect to drug content, particle size, residual solvents, initial in vitro release, and PK characteristics in rats. Drug was extracted to obtain a preliminary assessment of exendin-4 purity post-encapsulation in selected batches.

In Vitro Initial Release

The initial release of exendin-4 was determined by measuring the concentration of exendin-4 after 1 hour in release buffer (10 mM HEPES, 100 mM NaCl, pH 7.4).

150±5 mg of microspheres were placed in 5.0 mL of 10 mM HEPES, 100 mM NaCl, pH 7.4 buffer at room temperature, vortexed for about 30 seconds to suspend the solution and then placed in a 37° C. air chamber for 1 hour. After 1 hour, the samples were removed from the chamber and inverted several times to mix, followed by centrifuging at 3500 rpm for 10 minutes. The supernatant was removed and analyzed immediately by HPLC using the following conditions: Column: TSK-GEL®, 7.8 mm×30 cm, 5 m (TSOH BIOSEP PART #08540); Column Oven Temperature: Ambient; Autosampler Temperature: 6° C.; Flow Rate: 0.8 mL/minute; Detection: 280 nm; Injection Volume: 10 L; Mobile Phase: 35% Acetonitrile/65% Water with 0.1% TFA/liter (v/v); Run Time: Approximately 20 minutes. Exendin-4 bulk drug substance, 0.2 mg/mL prepared in 30 mM Acetate Buffer, pH 4.5, was used as a standard.

Animal Studies

All pharmacokinetic (PK) studies described herein were conducted in adult male Sprague-Dawley rats weighing approximately 500±50 g.

For PK characterization of the microparticle formulations, each animal received a subcutaneous injection of microparticles suspended in diluent (3% carboxymethylcellulose, 0.9% NaCl, 0.1% Tween 20) to the inter-scapular region. Generally, the dose was approximately 1.0 mg exendin-4 per rat in an injection volume of 0.75 mL. Blood samples were collected via lateral tail vein at 0.5, 2, 4, 6, 10, 24 hours, and 2, 4, 7, 10, 14, 17, 21, 24 and 28 days post-dose. Blood samples were immediately placed in MICROTAINER® tubes containing EDTA and centrifuged at about 14,000×g for about two minutes. Plasma was then transferred to MICROTAINER® tubes without additive and stored at −70° C. until time of assay. IRMA was used to determine plasma exendin concentrations.

In Vivo Release-IRMA

The method for quantifying exendin-4 in plasma is a sandwich immunoassay, with the analyte captured by a solid phase monoclonal antibody EXE4:2-8.4 and detected by the radio-iodinated monoclonal antibody GLP-1:3-3. Counts bound are quantitated from a standard calibration curve. This assay is specific for full length or intact exendin-4 and does not detect exendin-4 (3-39). A typical standard curve range is 30 pg/mL to 2000 pg/mL depending on the age of the tracer antibody.

In Vitro and In Vivo Release

Figure 6:
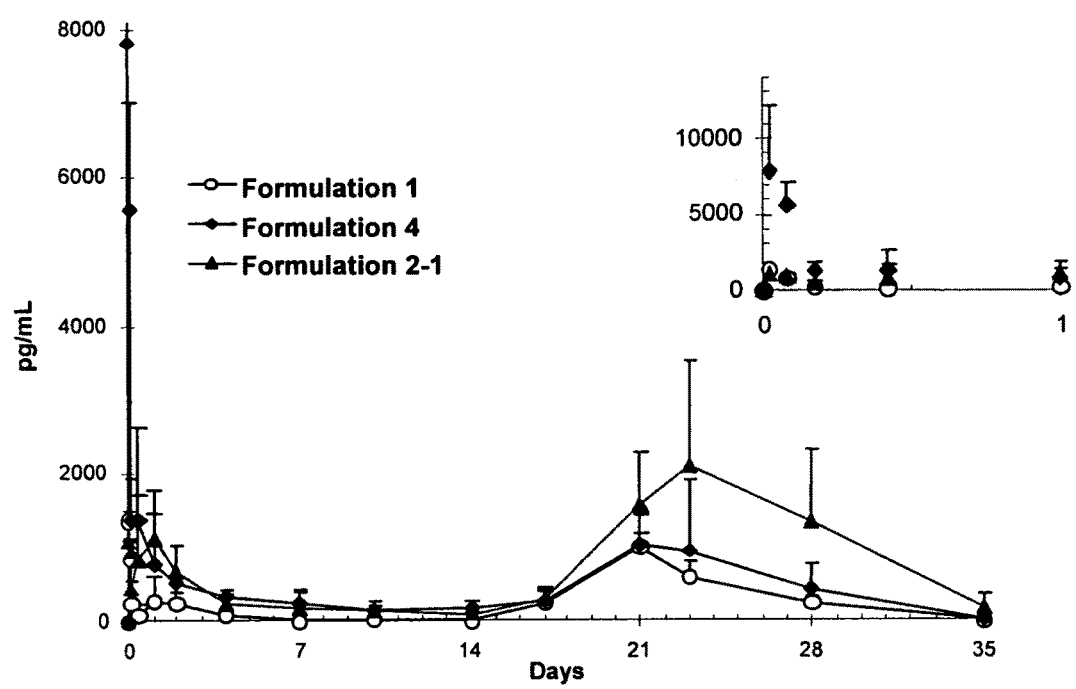
FIG. 6 is a representative pharmacokinetic curve (concentration, pg/ml v. time, days with inset showing concentrations over first day) for Formulation 2-1 (3% exendin-4 and 2% sucrose), Formulation 1 (3% exendin-4 alone) and Formulation 4 (3% exendin-4 and 0.5% ammonium sulfate).

Formulations 2, 2-1 and 2-2 (3% exendin-4 and 2% sucrose) were tested for initial release in vitro as described above. The in vitro release was 0.4%, 0.4% and 0.5%, respectively. All three batches also had a relatively low in vivo initial release in the range of 1154 to 1555 pg/mL for $C_{max}$ 0-1 day. FIG. 6 is a representative pharmacokinetic curve for the formulations having 3% exendin-4 and 2% sucrose_(2-1) and also for 3% exendin-4 alone (1) and 3% exendin-4 and 0.5% ammonium sulfate (4). A ratio of silicone oil-to-methylene chloride of 1.5:1 was used and the viscosity of the silicone oil was 350 cs.

From FIG. 6 it can be seen that the formulations not containing ammonium sulfate exhibit a lower initial release. Although the formulation having exendin-4 alone showed a suitable initial release the post encapsulation purity of the drug was decreased as compared to the formulation having the exendin-4 in combination with the sucrose. The addition of sugar in the formulations decreases degradation of the agent.

Figure 7:
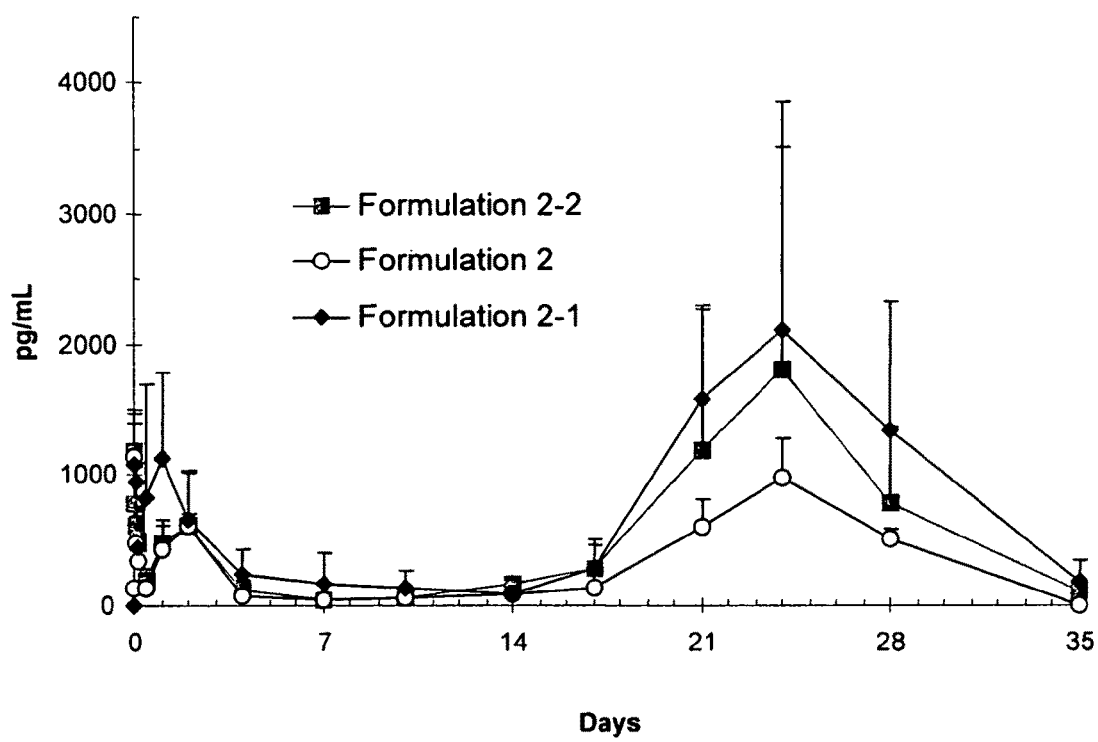
FIG. 7 is a graph of in vivo release profile for the three microparticle Formulations 2, 2-1 and 2-2.

The in vivo release profile for the three formulations 2, 2-1 and 2-2 compared above, are shown in FIG. 7. All three batches exhibited a relatively low initial release followed by a "trough" (low serum levels between about day 4 to day 17), followed by a sustained release over about day 21 to day 28. The low initial release and the shape of the release profile were consistent for the three formulations.

Formulation Using a 1:1 Ratio of Silicone Oil to Methylene Chloride

Formulations 2-3, 2-4 and 2-5 from Table 1 (3% exendin-4, 2% sucrose) were prepared using a 1:1 ratio of silicone oil to methylene chloride. The initial release was higher for these formulations than for formulations 2, 2-1 and 2-2 of Table 1 (3% exendin-4, 2% sucrose with a 1.5:1 silicone to methylene chloride ratio). Specifically the 1.5:1 ratio formulations provided an average initial release about 0.4%, whereas the 1:1 ratio formulations provided an average initial release about 1.0%. The same trend was observed in vivo with $C_{max}$ 0-1 day in rats was 2288±520 pg/mL for a 1:1 ratio, whereas the $C_{max}$ 0-1 day in rats was 1300±221 pg./mL for the 1.5:1 ratio.

Increased Drug Loading

Increasing the exendin-4 load to 4% while maintaining the sucrose at 2% resulted in an initial release in vitro and in vivo in the same range as for the 3% loading.

Figure 8:
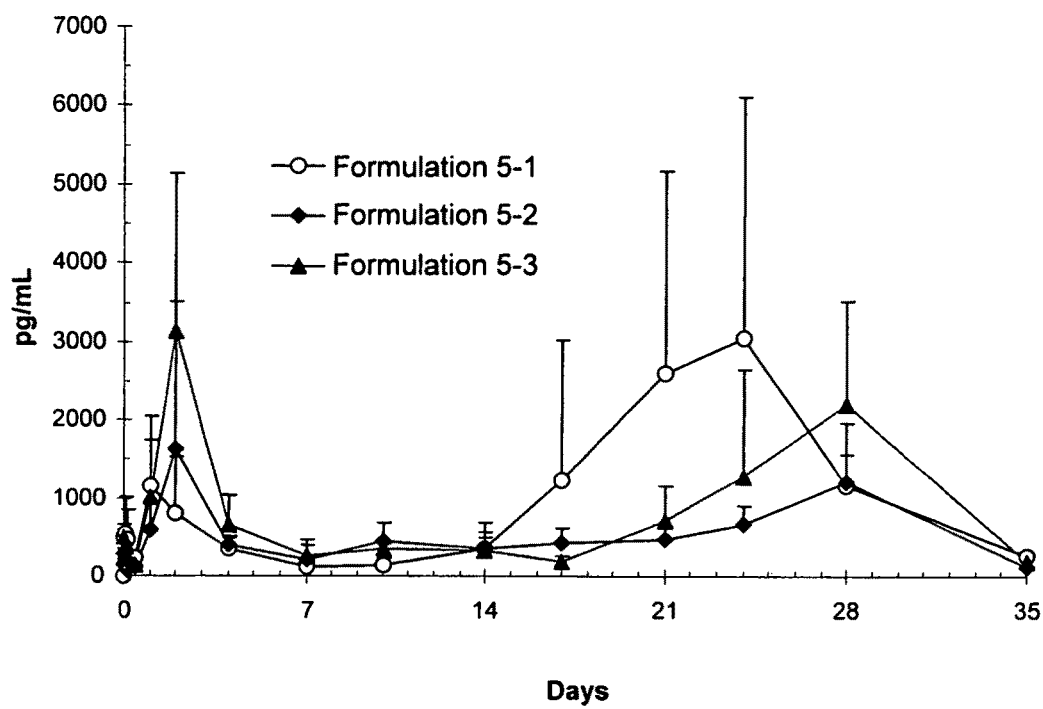
FIG. 8 is a graph of the pharmacokinetic data for microparticle Formulations 5-1, 5-2 and 5-3.

Three formulations of Type 5 from Table 1 were prepared (5% drug load, 2% sucrose, 1.5:1 silicone oil-to-methylene chloride ratio). The three batches, 5-1, 5-2 and 5-3 all exhibited a low in vitro initial release ranging from 0.2 to 0.5%. Similarly, the in vivo $C_{max}$ of the formulations was consistently low ranging from 467 pg/mL to 1267 pg/mL. FIG. 8 shows a graph of the pharmacokinetic data for the three batches tested. Compared to the behavior of the 3% exendin-4 formulation having 2% sucrose, the 5% formulations exhibited higher serum levels of drug over about day 1 and day 2. The remainder of the profile for the 5% formulations was similar to the 3% formulations having a trough followed by release of drug primarily over day 21 to day 28.

While this invention has been particularly shown and described with references to preferred embodiments thereof, it will be understood by those skilled in the art that various changes in form and details may be made therein without departing from the scope of the invention encompassed by the appended claims.

The invention claimed is:

1. An injectable composition for sustained release of a glucoregulatory polypeptide, comprising:
   a biocompatible polymer having the glucoregulatory polypeptide dispersed therein so as to be present at about 0.5 to 5% (w/w) of the weight of the composition, and a sugar dispersed therein so as to be present at about 0.1 to 5% (w/w) of the weight of the composition,
   wherein the injectable composition is free from additional ingredients that alter the rate of release of the glucoregulatory polypeptide from the injectable composition.

2. The injectable composition of claim 1, wherein the composition has a release profile in which the $C_{max}$ of the glucoregulatory peptide occurs between day 21 and day 28.

3. A method of treating a patient suffering from Type 2 diabetes, comprising administering a therapeutically effective amount of the injectable composition of claim 1.

4. A method of treating a patient suffering from a condition selected from the group consisting of Type 2 diabetes, impaired glucose tolerance, obesity, and cardiovascular disorder, the method comprising administering a therapeutically effective amount of the injectable composition of claim 1.

5. The method of claim 4, wherein the composition has a release profile in which the $C_{max}$ of the glucoregulatory peptide occurs between day 21 and day 28.

* * * * *